(12) United States Patent
Bass

(10) Patent No.: US 6,714,018 B2
(45) Date of Patent: Mar. 30, 2004

(54) METHOD OF COMMISSIONING AND OPERATING AN ELECTRICALLY HEATED PIPE-IN-PIPE SUBSEA PIPELINE

(75) Inventor: Ronald M. Bass, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/910,622

(22) Filed: Jul. 20, 2001

(65) Prior Publication Data

US 2003/0020499 A1 Jan. 30, 2003

(51) Int. Cl.⁷ .................... G01R 31/08; G01R 27/08
(52) U.S. Cl. ........................ 324/525; 324/721
(58) Field of Search ............... 324/718, 615, 324/525, 721; 392/311

(56) References Cited

U.S. PATENT DOCUMENTS

| | | | |
|---|---|---|---|
| 972,308 A | 10/1910 | Williamson | |
| 1,231,202 A | 6/1917 | Saylor | |
| 2,217,857 A | 4/1937 | Byck | 166/21 |
| 2,096,279 A | 10/1937 | Karcher | 255/28 |
| 2,178,720 A | 2/1939 | Daniels | 219/47 |
| 2,206,831 A | 3/1940 | Betrhelsen | 74/440 |
| 2,224,403 A | 12/1940 | Lines | 219/39 |
| 2,306,831 A | 12/1942 | Proctor | 219/39 |
| 2,660,249 A | 11/1953 | Jakosky | 166/17 |
| 2,678,377 A | 5/1954 | Justiz | 219/40 |
| 2,714,930 A | 8/1955 | Carpenter | 166/60 |
| 2,757,738 A | 8/1956 | Ritchey | 166/39 |
| 2,851,197 A | 9/1958 | Colton | 222/146 |
| 2,982,354 A | 4/1961 | Green | 166/60 |
| 3,184,958 A | 5/1965 | Eaton | 73/40.5 |
| 3,388,724 A | 6/1968 | Mowell et al. | 138/149 |
| 3,423,570 A | 1/1969 | Trabilcy | 219/301 |
| 3,432,186 A | 3/1969 | Braun | 285/53 |
| 3,439,075 A | 4/1969 | Bauer et al. | 264/45 |
| 3,507,330 A | 4/1970 | Gill | 166/248 |
| 3,515,837 A | 6/1970 | Ando | 219/10.49 |
| 3,547,193 A | 12/1970 | Gill | 166/248 |
| 3,556,218 A | 1/1971 | Talley, Jr. et al. | 166/265 |
| 3,605,888 A | 9/1971 | Crowson et al. | 166/248 |
| 3,614,986 A | 10/1971 | Gill | 166/303 |
| 3,620,300 A | 11/1971 | Crowson | 166/248 |
| 3,630,038 A | 12/1971 | Ando | 61/72.1 |
| 3,642,066 A | 2/1972 | Gill | 166/248 |
| 3,706,872 A | 12/1972 | Trabilcy | 219/300 |
| 3,789,188 A | 1/1974 | Rudbarg | 219/301 |
| 3,859,503 A | 1/1975 | Palone | 219/278 |

(List continued on next page.)

FOREIGN PATENT DOCUMENTS

| | | | |
|---|---|---|---|
| EP | 1070907 | 1/2001 | F16L/59/14 |
| GB | 2084284 | 7/1982 | F16L/53/00 |
| SU | 569815 | 9/1977 | |

(List continued on next page.)

OTHER PUBLICATIONS

"Direct Impedance Heating of Deepwater Flowlines," OTC 11037, May, 1999.

"Cable–Free Electrical Systems for the Oil to Gas Industry," Production Technologies Company, L.L.C., 600 Kenrick, Suite C–30; Houston, Texas 77060, advertisement, Copyright 1996, 6 pages.

(List continued on next page.)

*Primary Examiner*—N. Le
*Assistant Examiner*—Donald M. Lair

(57) ABSTRACT

Methods for determining electrical and thermal properties of a heated pipeline are provided. During commissioning or at any time thereafter, a base curve of impedance versus temperature of the pipeline is determined, so that impedance measurements can thereafter be used to measure temperature of the pipeline. Continuous monitoring of impedance is provided to detect changes in conditions of the pipeline. Start-up procedures that decrease risk of damage to the annulus from arcing are disclosed.

6 Claims, 2 Drawing Sheets

U.S. PATENT DOCUMENTS

| | | | |
|---|---|---|---|
| 3,885,595 A | 5/1975 | Gibson et al. | 138/155 |
| 3,933,031 A | 1/1976 | Uhlarik | 73/40.5 R |
| 3,935,632 A | 2/1976 | Maxson | 29/455 R |
| 3,944,262 A | 3/1976 | Stiner et al. | 285/53 |
| 3,958,636 A | 5/1976 | Perkins | 166/248 |
| 3,975,617 A | 8/1976 | Othmer | 219/300 |
| 3,981,181 A | 9/1976 | Ochiai | 73/40.5 R |
| 3,983,360 A | 9/1976 | Offermann | 219/301 |
| 4,010,799 A | 3/1977 | Kern et al. | 166/248 |
| 4,011,652 A | 3/1977 | Black | 29/455 R |
| 4,017,102 A | 4/1977 | Henderson | 285/53 |
| 4,140,179 A | 2/1979 | Kasevich et al. | 166/248 |
| 4,142,093 A | 2/1979 | Offermann | 219/301 |
| 4,319,632 A | 3/1982 | Marr, Jr. | 166/60 |
| 4,401,162 A | 8/1983 | Osborne | 166/248 |
| 4,450,711 A | 5/1984 | Claude | 73/40.5 R |
| 4,496,174 A | 1/1985 | McDonald et al. | 285/53 |
| 4,522,578 A | 6/1985 | Jameson et al. | 425/110 |
| 4,553,023 A | 11/1985 | Jameson et al. | 219/301 |
| 4,590,971 A | 5/1986 | Webster et al. | 138/149 |
| 4,644,780 A | 2/1987 | Jeter | 73/40.5 |
| 4,645,906 A | 2/1987 | Yagnik et al. | 219/301 |
| 4,667,505 A | 5/1987 | Sharp | 73/40.5 R |
| 4,684,786 A | 8/1987 | Mann et al. | 219/297 |
| 4,716,960 A | 1/1988 | Eastlund et al. | 166/60 |
| 4,768,455 A | 9/1988 | Maxson et al. | 114/264 |
| 4,831,324 A * | 5/1989 | Asakura et al. | 324/615 |
| 4,839,644 A | 6/1989 | Safinya et al. | 340/854 |
| 4,861,074 A | 8/1989 | Eastlund et al. | 285/53 |
| 4,874,925 A | 10/1989 | Dickenson | 249/301 |
| 4,970,467 A | 11/1990 | Burnett | 324/637 |
| 4,992,001 A | 2/1991 | Harrison | 405/166 |
| 4,996,879 A | 3/1991 | Kruka et al. | 73/592 |
| 5,072,622 A | 12/1991 | Roach et al. | 73/40.5 R |
| 5,172,730 A | 12/1992 | Driver | 138/104 |
| 5,189,374 A | 2/1993 | Burnett | 324/534 |
| 5,270,661 A | 12/1993 | Burnett | 324/527 |
| 5,289,561 A | 2/1994 | Filho | 392/478 |
| 5,421,675 A | 6/1995 | Brown et al. | 405/170 |
| 5,464,307 A | 11/1995 | Wilkins | 405/166 |
| 5,490,562 A | 2/1996 | Arnold | 166/267 |
| 5,605,798 A | 2/1997 | Koster | 435/6 |
| 5,801,953 A | 9/1998 | Thoma et al. | 364/487 |
| 5,836,719 A | 11/1998 | Martin et al. | 405/166 |
| 5,905,194 A | 5/1999 | Strong | 73/40.5 |
| 6,000,438 A | 12/1999 | Ohrn | 138/149 |
| 6,049,657 A | 4/2000 | Sumner | 392/469 |
| 6,058,979 A | 5/2000 | Watkins | 138/149 |
| 6,114,857 A | 9/2000 | Kohl | 324/534 |
| 6,142,707 A | 11/2000 | Bass et al. | 405/158 |
| 6,171,025 B1 | 1/2001 | Langner et al. | 405/154 |
| 6,179,523 B1 | 1/2001 | Langner et al. | 405/169 |
| 6,264,401 B1 | 7/2001 | Langner et al. | 405/169 |
| 6,278,095 B1 | 8/2001 | Bass et al. | 219/629 |
| 6,278,096 B1 | 8/2001 | Bass | 219/629 |
| 6,292,627 B1 | 9/2001 | Gilchrist, Jr. et al. | 392/311 |
| 6,305,429 B1 | 10/2001 | Welch et al. | 138/149 |
| 6,315,497 B1 | 11/2001 | Wittman et al. | 405/158 |
| 6,364,401 B1 | 4/2002 | Kim | 296/194 |
| 6,371,693 B1 | 4/2002 | Kopp et al. | 405/158 |
| 6,382,259 B1 | 5/2002 | Codling | 138/149 |
| 6,509,557 B1 | 1/2003 | Bass | 219/772 |
| 2003/0015519 A | 1/2000 | Stone, Jr. | 219/494 |
| 2003/0015436 A1 | 1/2003 | Bass et al. | 205/740 |
| 2003/0016028 A1 | 1/2003 | Bass | 324/642 |
| 2003/0017007 A1 | 1/2003 | Bass et al. | 405/154.1 |
| 2003/0020499 A1 | 1/2003 | Bass | 324/721 |

FOREIGN PATENT DOCUMENTS

| | | | |
|---|---|---|---|
| WO | 103122 | 4/1937 | |
| WO | 1359445 | 4/1972 | F16L/25/00 |
| WO | 1437587 | 7/1974 | F16L/13/10 |
| WO | 1532730 | 10/1976 | F16L/25/01 |

OTHER PUBLICATIONS

"Dunbar in Depth,"Offshore Engineer, Dec. 1994, 2 pages.

"Introduction to Direct Heating of Subsea Pipelines,"overview byStatoil, Saga Petroleum, CSO Norge, Alcatel, Kabel Norge and EFI, Feb. 1988.

"Monolithic Pipeline Electrical Isolation Joints," Hydro-Tech Systems, Inc., Engineered Pipeline Products, advertisement, Nov. 1996, 6 pages.

"New Double Pipe Insulated System (DPIS) Designed by Snamprogetti", Snamprogetti Offshore Division, Viale de Gasperi 16, San Donato Milanese, Milan, Italy, advertisement, 6 pages. no date.

"Skin Effect Pipe Heating Systems," Thermo Systems Technology, Inc. (TST), Four Commerce Park Square, 23200 Chagrin Boulevard, Suite 600, Beachwood, Ohio 44122, Copyright 1991, advertisement, 4 pp.

Stop Paraffin Build–up and Realize Your Well's Full Potential . . . Plug in Paratrol. International, Inc. (PTI), 15423 Vantage Parkway East, Houston, Texas 77032, advertisement, Copyright 1989, 6 pp.

"Tubing Casing Wireless Telemetry (Tucas System), " Schlumberger web page (1993?/Jun. 1996), 16 pages.

A. Anselmi et al., "TTDPIS: A New Underwater Technology in the Field of Traced Insulated Pipelines," 1994 OMAE, vol. 5, Pipeline Technology, ASME, 1994, pp. 69–76.

Anonymous, Insulated Pipe—Precision Engineering, Jun. 2000, The Bayou Bulletin, Issue #8 from www.bayoupip-.com/4News/Newslwtter0 8–4.thm, 2 pages.

Anonymous, "Insulated Technique to see first use in North Sea Development", May 17, 1993, Oil and Gas Journal vol. 91, Issue 20, p. 61.

B. J. Eastlund et al., "New System Stops Paraffin Buildup," Petroleum Engineer, Jan. 1989, 3 pages.

Brochure –Combi Pipe –the end of clogged pipelines, Alcatel Contracting Norway and Aker Engineering, 7 pages. 1991.

Brochure–World Wide Experience List –Compressed Gas Insulated Transmission Bus System Type CGIT, ABB Power T & D Company Inc., 30 Oak Street, Westborough, MA 01581, USA, 6 pages, Oct. 1996.

C. G. Langer, "Engineering Report—1979 Construction of the Cognac 12–inch Pipeline From Mississippi Canyon Block 194 to Southwest Pass East Bay Central Facilities, Offshore Louisiana," ES No. 74–82, Job No. 560513, Shell Oil Company, Pipeline Construction Department, *, 6 pages.

Compressed Gas Insulation Transmission Bus Ducts, ABB Power T&D Company, CGIT/PB Division, Westborough, MA, US 22 pages.

DeLuca, "Field of Dreams", Apr. 1, 2001, Offshore Engineering, form www.online.com/news/features/oe/2001 0401.Fields 0.520.asp, 9 pages.

F. Aarseth and E. Bentsen, "Heating of Pipelines, and Power Supply to Subsea Electrical Equipment," Aker Engineering a.s. A Bjømstad and B. Knutsen, Alcatel Contracting Norway a.s., DOT 1995, 23 pages.

F. R. Newbold and T. K. Perkins, "Wellbore Transmission of Electrical Power,", The Journal of Canadian Petroleum Technology, Jul.–Sep. 1978, Montreal, pp. 3–52.

F. G. Bosch, K. J. Schmitt, and B. J. Eastlund, "Evaluatoin of Downhole Electric Impedance Heating systems for Paraffin Control," Paper No. PCIC–90–34 presented at Industry Applications Society 37th Annual Petroleum and Chemical Industry Conference, Houston, Texas, Sep. 10–12, pp. 223–227, Sep. 10, 1990.

Fred S. Epstein and Gary L. White, "Understanding Impedance Heating, "Chemical Engineering, May 1996, pp. 112–118.

Gaylord, N.G., Gaylord Associates, Newark, New Jersey, "Polymers–Part I. Polyalklene Oxides and other Polyethers": Interscience Publishers: New York–London–Sydney, pp. 9–80, May 18, 1970.

"General Product Specification—Pipeline Insulating Joint," HydroTech Systems, Engineered Pipeline Products, advertisement, pp. Feb. –1995.

H. Collins and M.A.R. Lyle, Progress Reported in Design of Reelable Insulated Subsea Flow Lines, Oil and Gas Journal, Sep. 24, 1990, pp. 102–106.

K. H. Akfhampour, "A Novel Approach to Solving Downhole Fluid Flow Problems by Use of an Electric Heating System", Paper No. PCIC–85–35, 12 pages, 1985.

Krevelen, D. W., Univ. of Technology.Delft. The Netherlands, "Properties of Polymers", 3.sup.rd. Edition (Revised), Elsevier; Amsterdam–Oxford–New York–Tokyo, 1990; pp. 641–653.

M. I. Mollison, "Foam Insulation Gets First Reeled Installation off Australia," Oil and Gas Journal, May 18, 1992, pp. 80–82.

Monobloc Insulationg Joints Type "IK", No date.

N. B. Carson, "A New Method for Heat Tracing Long Pipelines," ASME, 74–Pet–35, paper presented at the Petroleum Mechanical Engineering Conference, Dallas, Texas, Sep. 15–18, 1974, pp. 2–4.

Protest Document, Dec. 8, 1987 letter of Andrew W. Marr, Jr. to the Assistant Commissioner of Patents requesting issuance of U.S. Pat. No. 4,716,960 available in the file history as of Jan. 5, 1988.

R. Wash, "Electromagnetic Energy Helps Recovery," Gulf Coast Oil World, Jun. 1986, pp. 18–19.

"Taking Induction Heating Underwater, "Process Heating, Jul./Aug. 1995, 1 page.

The Electrothermic Co. (TEC), 4916 Bear Lane, P.O. Box 4227, Corpus Christi, TX 78408 advertisement/sales brochure, 4 pages, No date.

Anedote–"Thermo Systems Under River Crossings" discussed in Supplemental Information Disclosure Statement filed on Jun. 22, 2000 for U.S. Pat. Application SN 08/921, 737, filed Aug. 27, 1997 entitled, "Method for Maintaining Well Fluids Within a Shut–In Subsea Pipeline".

Anecdote –"Fuel Oil Between Buildings" discussed in Supplemental Information Disclosure Statement filed on Jun. 22, 2000 for U.S. Pat. Application Ser. No. 08/921,727, filed Aug. 27, 1997, entitled "Method for Maintaining Well Fluids Within a Shut–In Subsea Pipeline".

Anecdote–"Asphalt Tranfer Liner from Tank Cars et al." discussed in Supplemental Information Disclosure Statement filed on Jun. 22, 2000 for U. S. Pat. Application Ser. No. 08/921,737, filed Aug. 27, 1997, entitled, "Method for Maintaining Well Fluids Within a Shut–In Subsea Pipeline".

Production Technologies Company Invention Discosure of R. M. Bass dated Jul. 24, 1986, "Disclosure for Controlled Paraffin Deposition in Subsea Pipelines" as discussed in Supplemental Information Disclosure Statement filed on Jun. 22, 2000 for U.S. Pat. Application Ser. No. 08/721,737, filed Aug. 27, 1997, entitled "Method for Maintaining Well Fluids Within a Shut–In Subsea Pipeline".

Purported Invention Disclosure of Production Technologies Company, L.L.C. (PTC) by Bernard J Eastlund and John Haeber, dated Apr. 28, 1995. "Apparatus for Introducing Electric Current into and Offshore Pipeline." 4 pages as discussed in Supplemental Information Disclosure Statement filed on Jun. 22, 2000 for U.S. Pat. Application Ser. No. 08/921, 737, filed Aug. 27, 1997, entitled "Method for Maintaining Well Fluids Within a Shut–In Subsea Pipeline".

* cited by examiner

METHOD OF COMMISSIONING AND OPERATING AN ELECTRICALLY HEATED PIPE-IN-PIPE SUBSEA PIPELINE

BACKGROUND OF THE INVENTION

1. Field of the Invention

The present invention relates to electrical heating of subsea pipelines. More particularly, the invention relates to method for commissioning and operating a pipe-in-pipe pipeline.

2. Description of Related Art

Offshore hydrocarbon recovery operations are increasingly moving into deeper water and more remote locations. Often satellite wells are completed at the sea floor and are tied to remote platforms or other facilities through extended subsea pipelines. Some of these pipelines extend through water that is thousands of feet deep, where temperatures of the water near the sea floor are in the range of 40° F. The hydrocarbon fluids, usually produced along with some water, reach the sea floor at much higher temperatures, characteristic of depths thousands of feet below the sea floor. When the hydrocarbon fluids and any water present begin to cool, phenomena occur that may significantly affect flow of the fluids through the pipelines. Some crude oils become very viscous or deposit paraffin when the temperature of the oil drops, making the oil practically not flowable. Hydrocarbon gas under pressure combines with water at reduced temperatures to form a solid material, called a "hydrate." Hydrates can plug pipelines and the plugs are very difficult to remove. In deep water, conventional methods of depressurizing the flow line to remove a hydrate plug may not be effective. Higher pressures in the line and uneven sea floor topography require excessive time and may create operational problems and be costly in terms of lost production.

The problem of lower temperatures in pipelines has been addressed by a variety of heating methods, including electrical heating. Most of the proposals for electrical heating of pipelines have related to pipelines on land, but in recent years industry has investigated a variety of methods for electrical heating of subsea pipelines. ("Direct Impedance Heating of Deepwater Flowlines," OTC 11037, May, 1999). One electrical heating method is the pipe-in-pipe method. In one configuration of a pipeline using this method, a pipe-in-pipe subsea pipeline is provided by which a flow line for transporting well fluids is surrounded concentrically by and electrically insulated from an electrically conductive outer pipe until the two pipes are electrically connected at the distal or remote end of a heated segment by a bulkhead. Voltage is applied between the inner and outer pipes at the proximate or electrical input end and electrical current flows along the exterior surface of the inner pipe and along the interior surface of the outer pipe. This pipe-in-pipe method of heating is disclosed, for example, in U.S. Pat. No. 6,142,707. Other variations of the general pipe-in-pipe method exist. The electrical power is supplied through an electrical isolating joint at the power input end of a segment of line to be heated. Alternating current, normally at about 60 Hz, is used. The voltage across the annulus is highest at the isolating joint and falls linearly to zero at the bulkhead. The current is essentially constant along the entire length of the pipe segment that is heated. Two key electrical effects, the skin effect and the proximity effect, confine the current flow largely to the annulus surfaces. Consequently, most of the current is effectively isolated from the produced fluids and the seawater around the pipeline.

Phenomena related to the commissioning (starting-up) and operation of pipe-in-pipe pipelines may cause loss of electrical isolation between the inside and outside pipes. This may be a result of water-induced arcing or a direct short because of inadvertent water or other contaminants entering the annulus or external mechanical damage. There is a need for methods that allow detection of any condition change in the pipeline that could cause an electrical fault upon application of power for heating and to allow operation of the pipeline by applying high voltages while minimizing risk of electrical faults.

SUMMARY OF THE INVENTION

In one embodiment, a method for determining electrical properties of a pipeline is provided. A base curve of impedance over the full range of operating voltages at a range of temperatures is developed. The curve may be used to measure thermal properties of the pipeline by measuring cooling rate. A method for applying voltage to the line provides increasing increments so that risk of damage from arcing is decreased.

DETAILED DESCRIPTION

U.S. Pat. No. 6,142,707 and U.S. patent applications filed concurrently herewith and entitled "Annulus for Electrically Heated Pipe-in-Pipe Pipeline," Ser. No. 09/910,696; "Power Supply for Electrically Heated Subsea Pipelines," Ser. No. 09/910,625; "Apparatus and Method for Electrical Testing Pipe in Pipe Pipeline," Ser. No. 09/910,295; and "Corrosion Protection of Electrically Heated Pipe-in-Pipe Subsea Pipeline," Ser. No. 09/910,489 all commonly owned, are hereby incorporated by reference herein.

Figure 1:
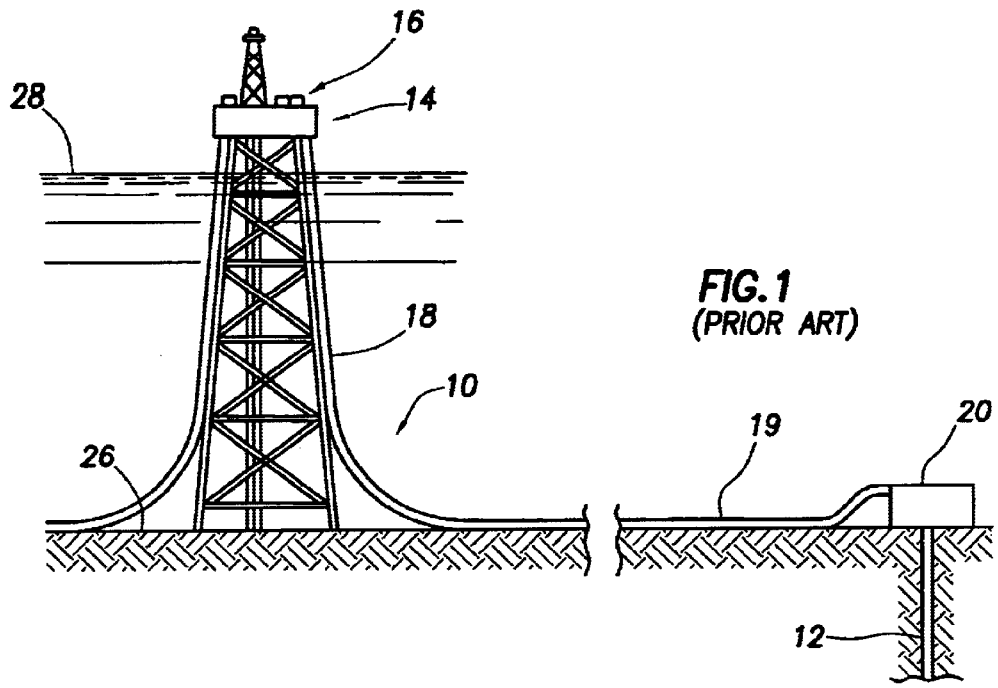
FIG. 1 shows the environment of use of a pipe-in-pipe pipeline.

FIG. 1 illustrates the environment of the present invention. Here remote satellite well 12 is connected to platform 14 with subsea flowline 10. Subsea flowline 10 includes seafloor section 19 and riser 18. Riser section 18 is connected to surface facilities 16 on platform 14. Seafloor section 19 may be 20 or more miles long, terminating at sled 20. Pipe-in-pipe flowline 10 may be composed of 40-ft joints of pipe welded together. In the embodiment shown in FIG. 1, individual 160 ft segments of pipe, called quads (four joints), are welded together to create pipe-in-pipe flowline 10. Seafloor section 19 is normally difficult to access, resting on seabed 26, which may be a half-mile or more below surface 28 of the ocean.

Surface facility 16 on platform 14 includes a power supply and associated control equipment for applying and controlling electrical power to the pipeline, as described in the patent application "Power Supply for Electrically Heated Subsea Pipeline," Ser. No. 09/910,625. Power may be applied at one end of the pipeline or at any intermediate point selected along the pipeline. The power requirements for heating a pipeline are often moderate in comparison with the power available on offshore platforms. If the equipment available on a pipeline is not capable of supplying the power needed, the platform must have provisions for adding electrical power supplies. A variable frequency drive for the electrical pipeline and an isolation transformer on the output of the power supply are preferred embodiments to meet the requirements of a power supply system.

Figure 2:
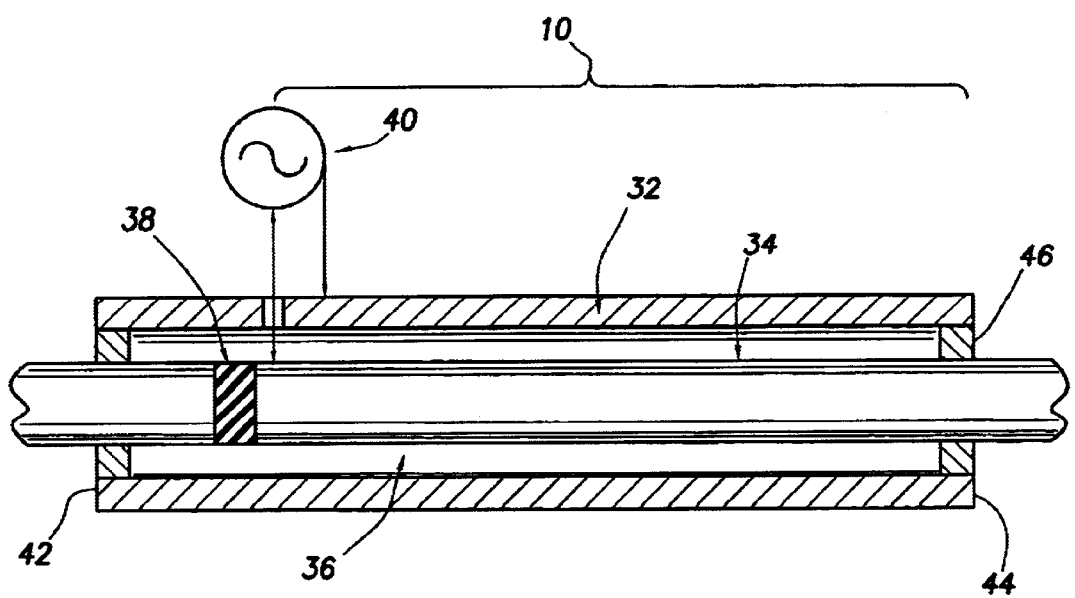
FIG. 2 shows a diagram of a power supply system suitable for electrical heating of a subsea pipeline.

FIG. 2 illustrates the pipe-in-pipe pipeline. Power supply 40 supplies voltage across annulus 36 between outer pipe 32 and inner pipe 34. Insulating joint 38, which is normally in proximity to platform 14, structurally joins and electrically insulates inner pipe 34 from outer pipe 32. Inner pipe 34 and outer pipe 32 are electrically joined at bulkhead 46.

To determine the power requirements for each heating mode of the pipeline, an electrical/thermal model of the pipeline is preferably developed. The power requirements for heating and for holding the temperature at specific values are determined using well-known energy balance and heat loss calculations. Measurements of electrical impedance of each segment of the pipeline before it is joined and placed on the sea floor are made. These measurements may be made by applying electrical voltage and measuring current flow on a selected number of segments of the pipe while it is still in preparation for laying. Procedures used for measuring electrical characteristics of the pipe are described in the patent application entitled "Apparatus and Method for Electrical Testing of Electrically Heated Pipe-in-Pipe Pipeline," Ser. No. 09/910,295 filed concurrently herewith. Using these measurements, the electrical resistance of the pipeline to be heated and the system power factor may be calculated.

Figure 3A:
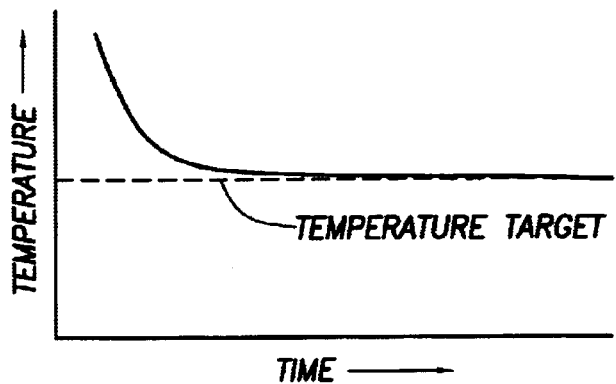
FIG. 3 shows graphs of temperature and time for (a) holding a pipeline at a target temperature and (b) heating a pipeline to a target temperature.

Commissioning and operation of the pipeline can be divided into four phases: (1) commissioning or startup, (2) monitoring condition of the line without heating, (3) heating to hold the line at a specified target temperature, for example, to prevent hydrate formation within the pipeline, and (4) heating to unplug the pipeline. Modes (3) and (4) are illustrated in FIGS. 3(a) and (b). In FIG. 3(a) temperature after a line is shut-in is illustrated. Power may be applied when the line is shut in, preferably with no waiting time. This mode of operation may be used on every shutdown or after shutdown has caused a selected amount of cooling. The holding temperature is selected to allow continued flow through the pipeline. Only enough power would be required to replace the heat lost from the carrier pipe in the absence of electrical heating at the same temperature.

Figure 3B:
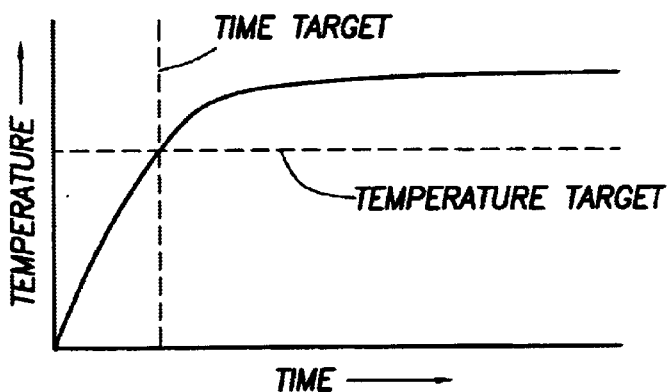

FIG. 3(b) illustrates temperature of the pipeline vs. time after the line has cooled below the temperature that is necessary to insure flow. The line may be plugged or at least exists at a temperature that could cause plugging and is then to be placed in the heating mode. This mode (mode 4) may be necessary, for example, after a hurricane shutdown. The line must be heated from a temperature as low as temperature at the sea floor to above the hydrate dissociation temperature. This heating should be accomplished within a specified time, preferably not more than a few days. This mode will require the highest electrical power.

The power requirements for heating in modes (3) and (4) are determined by initial and final temperatures, heating time, thermal insulation in the annulus, fluid in a hydrate (if present) and thermal properties of fluids and construction materials. The fraction of a hydrate plug that must be melted to unplug a pipeline will not be known. Calculations may be performed using techniques well-known in industry. The voltage and current that must be applied to the system to achieve the desired dissipation in the carrier pipe are calculated as discussed above.

Results of calculations using measured electrical properties of selected segments of the pipeline before installation and properties after installation are shown in Table I for two pipelines. Pipeline 1 is 7.74 miles long and Pipeline 2 is 6.25 miles long. Results for heating mode (mode 4:) calculations and holding mode (mode 3) calculations are shown. The system voltage is voltage at the power input end of the pipeline. Dimensions of the pipelines and other results are also shown in the table.

The temperature and heating time targets are set for the lowest impedance pipe joint, because it heats the least. In this calculation the lowest impedance joint is assumed to have a hydrate in it with a melting temperature of 60° F. The Heating time is based on 100% melting, but different percentage melting values may be used. The average pipe will heat more because it is higher impedance. The temperature shown for the minimum impedance pipe assumes that it contains a hydrate. However, most of the pipe does not have hydrates and so will heat much more. The highest impedance joint, with no hydrate present, would heat the most. These temperatures are not shown. The heating rate and time must be controlled so that the highest impedance pipe joints will not get so hot as to damage the insulation materials. In the systems described in Table I, a maximum current of 350 amperes, shown for Pipeline 1 and Pipeline 2 in the heating mode, would prevent this damage.

TABLE 1

ELECTRICAL REQUIREMENTS

|  | Pipeline 1 | | Pipeline 2 | |
| --- | --- | --- | --- | --- |
|  | Heating | Holding | Heating | Holding |
| System voltage | 2169 | 1285 | 1752 | 1037 |
| System current | 350 | 243 | 350 | 243 |
| System MVA | 0.76 | 0.31 | 0.61 | 0.25 |
| System power - watts | 575,688 | 225,758 | 464,864 | 182,298 |
| System power factor | 0.760 | 0.723 | 0.759 | 0.723 |
| Minimum temperature difference, ° F. | 60 | 45 | 60 | 45 |
| u-value, BTU/ft$^2$-hr ref inner pipe wall | 0.18 | 0.18 | 0.18 | 0.18 |
| Inner pipe OD, inches | 6.625 | 6.625 | 6.625 | 6.625 |
| Inner pipe wall thickness, inches | 0.625 | 0.625 | 0.625 | 0.625 |
| Outer pipe id, inches | 9.87 | 9.87 | 9.87 | 9.87 |
| Length, miles | 7.74 | 7.74 | 6.25 | 6.25 |
| Heating time, days | 4.2 | 100 | 4.2 | 100 |

After flow line installation and before starting operations, commissioning procedures may be used to assure that the pipeline heating system will operate correctly in modes 3 and 4 and to determine expected performance of the heating system. The pipeline is filled with water. A low voltage may be applied to the pipeline to test the monitoring mode of operation (Mode 2). The current flow at a range of applied voltages is measured. These data can be used to develop a baseline that may be used to detect changes caused by water influx into the annulus or other physical changes during the lifetime of the pipeline.

The pipeline may then be operated briefly over the entire range of power supply current and voltage that can be applied. The current and power factor are preferably recorded at each voltage setting and compared with predicted values.

The line is next heated to a target hold temperature, such as illustrated in FIG. 3(a). At this temperature, heating is stopped and current and voltage measured over the range of operating voltage. These measurements may be taken at several different temperatures as the line is heated or cooled. Then the line is further heated to the higher temperature target indicated in FIG. 3(b) and the voltage-current measurements over the range of operating voltage are repeated. These data at the different temperatures give the system temperature dependence of impedance. Also, during heating, leakage current may be monitored on the pipeline and any umbilical connections to the pipeline at each heating current level applied using measurements described in the patent application entitled "Corrosion Protection of Electrically Heated Pipe-in-Pipe Subsea Pipeline," Ser. No. 09/910,489 filed concurrently herewith. The heating and cooling cycle may be executed two or more times to validate heating and cooling rates as a function of the applied power and to develop data from which measurements of current and voltage can be used for measuring temperature of the pipeline.

Figure 4:
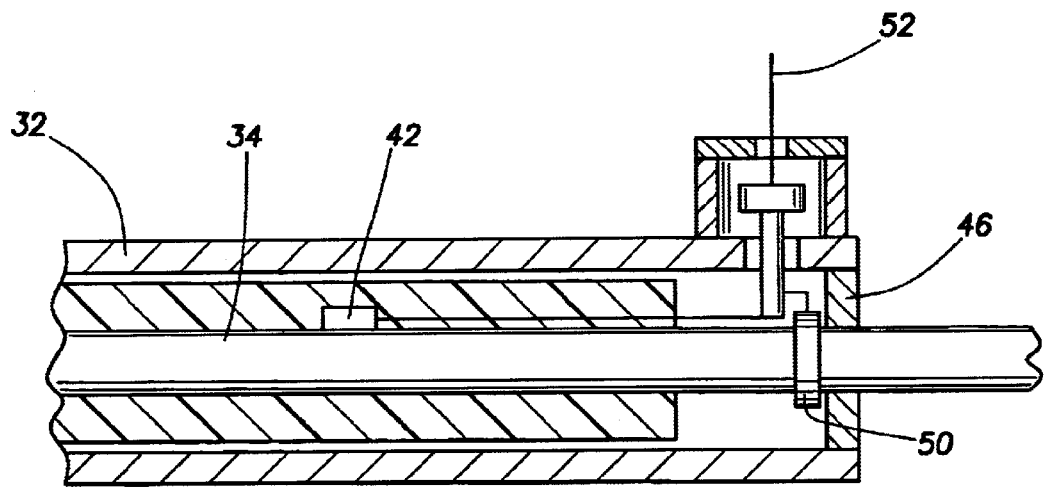
FIG. 4 shows a cross-section of apparatus for measuring temperature and electrical current in the pipeline near the bulkhead of an electrically heated pipeline and transmitting data obtained.

Temperature measurements of the pipeline during heating and cooling cycles can be used to calculate heat loss and insulation characteristics of the pipeline. In addition to temperature measurements based on impedance measurements of the pipeline, one or more temperature sensors, such as thermocouples, may be attached to the pipeline. The temperature sensors may be attached near the bulkhead, under insulation on the inside pipe, as shown in FIG. 4. Temperature sensor 42 contacts inside pipe 34 and is electrically connected through the wall of outer pipe 32. The connection is then connected to the control module pipeline termination sled 20 (FIG. 1), which in turn is connected to the umbilical at the wellhead of well 12. Data are then transmitted to a control point for the system, which is normally on the platform where the power supply is located. In a second cool down cycle, a closed loop control test may be run using such temperature sensor. If the temperature sensor is not operative, the power level required to hold the target temperature is calculated based on the insulation value and pipe impedance and the system is run on power control. If the temperature sensor is operative, during heating and cooling tests temperature data may be collected to validate the calculated power requirements.

A gross fault could be caused by flooding of the annulus due to a breach of the outer pipe, excess water introduced during welding of the pipe or other annulus contamination during construction or external damage causing a large displacement of the outer pipe wall. Quality assurance procedures may be provided to test for fault conditions during operations. The rate of temperature increase during application of power, as indicated by the temperature sensor, or lower than expected temperature of the line at the temperature sensor during flowing conditions may be used to indicate whether all the current is reaching the end of the flow line. A low temperature during flow will indicate flooding in the annulus. Also, impedance of the pipeline may be monitored, since a fault anywhere except near the bulkhead of the line will cause a detectable change in system impedance. Also, periodic time domain reflectometer tests, as described in the concurrently filed application "Apparatus and Method for Electrical Testing Pipe in Pipe Pipeline," Ser. No. 09/910,295, may be used to identify short circuit fault conditions, but not locations with low breakdown voltage that are not shorted. The time domain reflectometer measurements may not reach the end of the flow line, due to attenuation and dispersion of the pulse wave form. Finally, the pipe current may be monitored at the bulkhead, using the current transformer 50 (FIG. 4) near the bulkhead. Preferably, a signal channel is provided to communicate temperature measurements and measured current from the bulkhead to a control location. Such current may be used as a sensitive detector of gross fault conditions anywhere in the pipeline while power is applied, and will indicate during either flowing or shutdown conditions.

During normal flowing operation of a pipeline, when heating is not required, a low voltage is preferably maintained on the pipeline. This allows continuous monitoring of the power supply and the system impedance, while minimizing power consumption and electrical stress on the annulus and other equipment. A change in impedance of the pipeline can then be used as an indicator of an electrical fault in the annulus. This voltage may be any voltage but conveniently is in the range from about 100 volts to about 300 volts.

Arcs between the inner and outer pipes can be sustained while drawing a current of only a few hundred milliamperes, which is too small to be detected at the power supply. Such arc may be sustainable for a long period without producing damage to the pipes, but there is some unknown level of risk of damage. Therefore, power should not be applied if arcs are detected.

During startup of heating of the pipeline, whether in mode 3 or mode 4, voltage is increased in small increments, such as about 400 volts. With each increase, voltage is preferably applied for only a few seconds (in the range of about 5 seconds) and then shut off for about the same time. This process is continued until the operating voltage is reached, which normally will require about 1 minute. If small amounts of water are present in the annulus where the water may cause arcing, this procedure allows any arcs that form in the annulus to flash off the water causing the arcs without doing excessive damage to the insulating surfaces. The arc is then extinguished when power is removed. The evaporated water recondenses on the coolest surface in the annulus, which is the outer pipe wall. The water can then run down into a water seal, where it can be safely collected. This procedure is preferably used every time power is applied to the flow line, but at a minimum should be applied the first time the line is powered.

During a normal shutdown of the pipeline, heating will be applied when the pipe is at risk of cooling to hydrate formation temperature. Alternatively, heating may be applied whenever there is a shutdown of flow in the pipeline. In another embodiment, power may be controlled by a temperature sensor attached to the pipeline, such as sensor 42 in FIG. 4. In another embodiment, the line is run on constant power control, constant current control or constant voltage control, i.e. controlled on electrical input without use of temperature measurements.

If the pipeline is allowed to cool to sea floor temperature, a heating time at full power to assure complete melting of hydrates is preferably not more than about five days. Since the hydrate plug may not occur in a quad or a part of the pipeline equipped with a thermocouple, there is no feedback signal to determine when a hydrate plug is fully melted. Therefore, heat must be applied for a predetermined period of time. If it is acceptable to flow with a partly melted hydrate plug, pressure may be applied to the pipeline in an attempt to cause flow periodically during the heating process. Flow can proceed as soon as the plug allows fluid to pass through the pipeline. Alternatively, the minimum time required to melt a specified fraction of the plug can be calculated and flow can be initiated after that time has elapsed.

Heating requirements are estimated based on the assumption that the hydrate forms in the lowest impedance measured during pipeline testing. However, there may be significant convective heat transfer along the line. Further, it is likely that a partially melted hydrate plug would quickly break-up if flow were initiated. Therefore, flow may be attempted within a short time, for example, a day of heating of the pipeline, since partial melting in the inner pipe may be sufficient to initiate flow.

While particular embodiments of the present invention have been described, it is not intended that these details should be regarded as limitations on the present invention, except to the extent that they are included in the appended claims. It should be understood that various changes, substitutions and alterations can be made hereto without departing from the spirit and the scope of the invention as defined by the appended claims.

What is claimed is:

1. A method for determining electrical and thermal properties of an electrically heated pipe-in-pipe pipeline, comprising:

at a first temperature, applying a range of voltage to the pipeline and measuring impedance over the range of voltage to establish a baseline range of impedance for the pipeline at the first temperature.

2. The method of claim 1 further comprising heating the pipeline to a selected second temperature and applying a range of voltage to the pipeline and measuring impedance over the range of voltage to establish a baseline range of impedance for the pipeline at the second temperature.

3. The method of claim 2 further comprising the step of heating the pipeline to a selected number of temperatures and applying a range of voltage to the pipeline and measuring impedance over the range of voltage to establish a baseline range of impedance for the pipeline over a selected temperature range.

4. The method of claim 1 further comprising the step of measuring leakage current of the pipeline.

5. The method of claim 3 further comprising the step of heating the pipeline to a selected temperature and measuring temperature by measuring a first electrical impedance of the pipeline, shutting off electrical power and allowing the pipeline to cool for a selected time, measuring temperature by measuring a second electrical impedance of the pipeline to determine a rate of temperature change, and calculating a thermal property from the rate of temperature change.

6. The method of claim 1 wherein the range of voltage is in the range from zero to about the maximum operating voltage of the pipeline.

* * * * *